US006184042B1

(12) United States Patent
Neumann et al.

(10) Patent No.: US 6,184,042 B1
(45) Date of Patent: Feb. 6, 2001

(54) METHOD FOR REDUCING HOOK EFFECT IN AN IMMUNOASSAY

(75) Inventors: Ulrich Neumann, Weilheim; Helmut Lenz, Tutzing; Norbert Franken, Starnberg, all of (DE)

(73) Assignee: Boehringer Mannheim GmbH, Mannheim (DE)

( * ) Notice: Under 35 U.S.C. 154(b), the term of this patent shall be extended for 0 days.

(21) Appl. No.: 08/862,062

(22) Filed: May 22, 1997

(30) Foreign Application Priority Data

May 24, 1996 (DE) ........................................ 196 21 133

(51) Int. Cl.[7] ........................ G01N 33/543; G01N 33/53; G01N 33/542; G01N 33/537

(52) U.S. Cl. ............................ 436/518; 435/7.1; 435/7.9; 435/7.92; 435/7.94; 435/7.93; 435/962; 436/523; 530/387.3

(58) Field of Search ............................ 435/7.1, 7.9, 7.92, 435/7.93, 7.94, 962; 436/518, 523; 530/387.3

(56) References Cited

U.S. PATENT DOCUMENTS

| | | | | |
|---|---|---|---|---|
| 4,885,255 | * | 12/1989 | Stock et al. | 436/512 |
| 5,188,939 | * | 2/1993 | Mangold et al. | 435/7.92 |
| 5,273,743 | * | 12/1993 | Ahlem et al. | 424/85.8 |

OTHER PUBLICATIONS

Harlow et al. "Antibodies, A laboratory Manuel" Cold Spring Harbor Laboratory. pp. 553–612, 1989.*

* cited by examiner

*Primary Examiner*—Yvonne Eyler
*Assistant Examiner*—Jennifer Nichols
(74) *Attorney, Agent, or Firm*—Fulbright & Jaworski, LLP

(57) ABSTRACT

In order to extend the measuring range and to reduce the Hook effect in an immunological method of determination of an antigen based on the principle of a sandwich assay it is preferable to use a method which is characterized in that the labelled detection molecule is an oligomer of a binding molecule selected from antibody or/and antibody fragment.

19 Claims, No Drawings

METHOD FOR REDUCING HOOK EFFECT IN AN IMMUNOASSAY

DESCRIPTION

The present invention concerns a method for the immunological determination of an analyte according to the sandwich assay principle and suitable binding substances for this. In particular the invention concerns an improvement of such sandwich methods in order to extend the measuring range and to reduce the Hook effect.

The quantitative determination of antigenic substances by means of immunoassays is known. A so-called sandwich assay is often used for this in which two antibodies directed towards the same or different epitopes of the analyte are incubated with a sample containing an analyte to be determined. In this method a first soluble antibody is directly or indirectly coupled to a signal-generating system i.e. a label whereas a second antibody (in a heterogeneous assay) is present coupled to a solid phase or is provided with a binding component such as e.g. biotin which is capable of binding to an appropriately coated solid phase.

The concentration of a number of diagnostically important proteins can vary within a wide range which means a wide measuring range is desirable or even essential for the analytics. Examples of such proteins are e.g. cancer parameters such as α fetoprotein (AFP) and carcinoembryonic antigen (CEA) and also the pregnancy protein human chorionic gonadotropin (HCG). When determining such analytes it is diagnostically important on the one hand to obtain an exact value in high concentration ranges in order to be able to carry out a successful monitoring but on the other hand it must also be possible to carry out an exact determination in the lower concentration range for a qualitatively correct diagnosis (yes/no) which in turn can lead to fundamental therapeutic consequences.

A problem with high analyte concentrations in a sample to be examined is the so-called "Hook effect" which is understood as a decrease of the detectable signal at very high analyte concentrations. The reason for this is that normally in a heterogeneous sandwich assay format the soluble antibody and the solid phase antibody are present in an excess relative to the analyte to be determined so that the sandwich complexes can be formed and also detected essentially completely; however, in the case of a high analyte concentration a limited number of antibodies is faced by a very large number of analyte molecules. In the extreme case there is a deficit of solid phase antibody so that the analyte is only partially bound and moreover the fraction of analyte bound to the solid phase cannot be completely detected since labelled antibody is captured by the excess of analyte with formation of soluble detection antibodies: analyte complexes. This results in a reduction of the measured signal which can lead to a false negative test result.

One solution to the problem is of course to adequately dilute the sample to be examined. However, since in practice it is not known from the start when and to what extent a dilution has to be carried out, this means that several measurements with different concentrations have to be carried out which is undesirable for reasons of costs and because of the increased amount of work.

A further solution to this problem is to increase the concentration of both antibodies used in the sandwich assay. This however, results in a number of disadvantages such as for example additional possibilities of interference, a high blank value and an unfavourable shape of the calibration curve. Moreover the costs of each individual determination are also increased so that this possibility can also not be regarded as satisfactory.

Yet a further solution is disclosed in U.S. Pat. No. 4,743,542. This patent teaches that the calibration curve can be linearized at high analyte concentrations by addition of unlabelled first or second antibody or of mixtures thereof. This lowers the sensitivity in the lower measuring range but increases it at higher analyte concentrations resulting in an overall linearization of the calibration curve.

However, a disadvantage of the method according to U.S. Pat. No. 4,743,542 is the reduction of the sensitivity in the lower measuring range. Such a reduction is particularly critical when an accurate test result is essential in the lower measuring range for example in the HCG test in order to determine whether a pregnancy is present or not.

Hence the object of the invention was to provide a method for the immunological determination of an analyte in which the disadvantages of the state of the art are at least partially eliminated and which in particular enables a quantitatively exact determination over a wide measuring range while at the same time obtaining good results in the lower concentration range.

This object is achieved according to the invention by a method for the immunological determination of an analyte in a sample liquid according to the principle of a sandwich assay in which the sample liquid is incubated in the presence of a solid phase with at least two receptors capable of binding to the analyte to be determined in which the first receptor is soluble and the second receptor (a) is bound to a solid phase or (b) is capable of binding to a solid phase and the analyte is detected by determining the label in the solid phase or/and in the liquid phase which is characterized in that the first receptor is an oligomer of a binding molecule selected from antibodies, antibody fragments and mixtures thereof.

It has surprisingly turned out that the use of a soluble oligomeric antibody enables the Hook effect to be reduced and hence an extension of the measuring range. In general the sensitivity in the lower measuring range is retained or even improved. The lower limit of detection LLD according to Kayser (Fresenius "Zeitschrift für analytische Chemie", volume 209, number 1, page 1–18, 1965) is used in the present description as a measure of the sensitivity in the lower measuring range.

The first receptor used according to the invention is an oligomer of a binding molecule selected from antibodies or/and antibody fragments and for the sake of simplicity is referred to as "oligomeric antibody" in the following. The prefix "first" or "second" antibody only serves the purpose of distinction in this description and does not for instance refer to an order of addition etc. The term "antibody" in the present invention is understood as an antibody with a single specificity such as a monoclonal antibody as well as a mixture of antibodies which are directed towards different epitopes of the same antigen such as a polyclonal antiserum. "Antibody fragment" is understood as any molecule which is derived from a complete antibody while retaining at least one paratope and which can for example be obtained by enzymatic or chemical treatment of an antibody or by genetic engineering. In particular an $F(ab')_2$ fragment is understood as an antibody fragment.

The degree of oligomerization relative to a complete antibody or to an $F(ab')_2$ fragment is at least two i.e. the minimum number of paratopes of an oligomeric antibody according to the invention is four. The minimum degree of oligomerization is preferably two to three. The maximum degree of oligomerization is up to 15, preferably up to 10 and more preferably up to 8. The degree of oligomerization is most preferably 2 to 8 and especially preferably 4 to 6.

The oligomeric first receptor is preferably used in a labelled form in the method according to the invention. This means that it is coupled directly or indirectly to a labelling group. In this connection a direct coupling is understood as a covalent incorporation of a detectable substance or of a molecule which on reaction with a suitable substrate generates a detectable substance. An example of the latter would be for example an enzyme which is covalently bound to the receptor optionally via a spacer. An indirect coupling denotes a configuration in which the first receptor according to the present invention and a detectable substance or a molecule that generates such a substance are capable of binding to one another via a specific binding pair such as biotin/avidin.

The labelling group in the method according to the invention can be selected from known labels in the state of the art. Examples are radiolabels and enzyme labels or luminescent labels. Preferred examples of enzyme labels are e.g. alkaline phosphatase, peroxidase and galactosidase. Preferred as luminescent labels are photoproteins that can be activated by calcium such as aequorin and electrochemiluminescent labels. Labels in which the determination is by means of a luminescent reaction are especially preferred and a luminescent metal chelate labelling group is most preferred as the labelling group.

Luminescent metal chelates are metal chelates which generate a detectable luminescence reaction. The detection of this luminescence reaction can for example be by measurement of fluorescence or by electrochemi-luminescence. The metal of these metal chelates is for example a transition metal or a rare earth metal. The metal is preferably ruthenium, osmium, rhenium, iridium, rhodium, platinum, indium, palladium, molybdenum, technetium, copper, chromium or tungsten. Ruthenium, rhenium, iridium and osmium are particularly preferred and ruthenium is most preferred.

The ligands which form the metal chelate together with the metal are usually polydentate ligands i.e. ligands with several coordination positions. Polydentate ligands for example comprise aromatic and aliphatic ligands.

Suitable aromatic polydentate ligands include aromatic heterocyclic ligands. Preferred heterocyclic ligands are N-containing polyheterocycles such as e.g. bipyrididyl, bipyrazyl, terpyridyl and phenanthrolyl. These ligands can for example contain substituents such as alkyl, substituted alkyl, aryl, substituted aryl, aralkyl, carboxylate, carboxyaldehyde, carboxamide, cyano, amino, hydroxy, imino, hydroxycarbonyl, aminocarbonyl, amidine, guanidinium, ureide, groups containing sulphur, groups containing phosphorus and the carboxylate esters of N-hydroxysuccinimide. The chelate can also contain one or several monodentate ligands. Examples of monodentate ligands include carbon monoxide, cyanides, isocyanides, halogenides and aliphatic, aromatic and heterocyclic phosphines, amines, stilbenes and arsines.

The luminescent metal chelate is particularly preferably selected from metal chelates containing bipyridyl or phenanthrolyl ligands. Examples of suitable metal chelates and the production thereof are described in EP-A-0 178 450, EP-A-0 255 534, EP-A-0 580 979 and WO 90/05301. Reference is hereby made to this disclosure. The most preferred metal chelates are ruthenium-(bipyridyl)$_3$ chelates. These chelates are commercially available in the form of active ester derivatives e.g. from Igen Inc. (Rockville, Md., USA).

The labelled receptor used in the method according to the invention contains one or several labelling groups. If several labelling groups are used per molecule of the first oligomeric receptor, it is preferred that the number of labelling groups is 2 to 20 and more preferably more than 2 to 10.

The second receptor used in the method according to the invention is bound to the solid phase or capable of binding to it. The term "bound to the solid phase" is understood in this description as an immobilization that takes place before the assay by attachment to a macromolecular carrier such as by adsorption, covalent binding or by means of a specific binding pair. Accordingly the term "capable of binding" is understood as an immobilization during the assay by means of the specific interaction of a suitable specific binding pair such as biotin/avidin. The second receptor is preferably coupled to the solid phase by means of a specific binding pair. The second receptor is particularly preferably biotinylated and the solid phase is coated with avidin or/and streptavidin.

The type of the second receptor is not particularly critical in the method of the present invention and hence the second receptor can be selected from a number of molecules provided that they can specifically bind to the analyte to be determined. Examples of substances which are suitable for use as a second receptor are for example oligomeric antibodies within the sense of this invention, antibodies, antibody fragments, cell receptors, enzymes, nucleic acids and other substances which due to a particular spatial structure or chemical affinity are capable of binding the analyte to be determined.

Depending on the exact experimental design conventional solid phases are used as the solid phase in the method according to the invention. These for example comprise finely dispersed materials such as polystyrene beads or particulate magnetic material and in general surfaces of reaction vessels such as the wall of a cuvette or a microtitre plate and for special applications chips, sensors or membranes. In the presently preferred embodiment of the method according to the invention the solid phase is particulate magnetic material which contains a coating capable of binding to the second receptor.

The exact procedure for the method according to the invention corresponds to known protocols of sandwich assays and is familiar to a person skilled in the art. In general a sample containing an analyte to be determined is incubated under suitable conditions and for an adequate time period with a first receptor, second receptor and solid phase in an arbitrary order in order to ensure that an immobilized sandwich complex forms. Subsequently the sandwich complex containing the analyte that forms is separated from free labelled antibody and determined qualitatively or quantitatively optionally after addition of a suitable detection substrate.

In a preferred embodiment of the method according to the invention the sample to be examined is firstly mixed and incubated with a ruthenium chelate labelled oligomeric antibody and a biotinylated antibody. In a second step magnetic beads which are coated with avidin or streptavidin are added and it is further incubated. Afterwards the mixture is passed over a magnet, the beads are separated i.e. the complex that forms is separated from the remaining sample and from non-bound labelled antibody and the separated complex is washed again with a solution which contains a reducing agent such as tripropylamine (TPA) and optionally a surface active agent. The washing process removes all the ruthenium except for that bound in the sandwich complex.

The measured Ru concentration is thus directly proportional to the analyte concentration. When an electrical voltage is applied a luminescence reaction occurs in which the ruthenium and the TPA react.

Optionally when using a labelled first receptor, an unlabelled analyte-specific receptor may be additonally present e.g. an unlabelled monomeric antibody or/and oligomeric antibody.

According to a further aspect the present invention concerns an oligomeric antibody comprising a conjugate of at least two antibodies, antibody fragments and mixtures thereof wherein the binding molecules are directly covalently linked together and which is characterized in that the degree of oligomerization is 2 to 15.

A direct linkage of the binding molecules means that the antibodies or antibody fragments are either linked together via a simple chemical bond or via a suitable bifunctional linker/spacer molecule. A large number of methods of accomplishing this and suitable spacer molecules are known to a person skilled in the art. For example bis(maleinimido)-methyl ester, dimethyl suberimidate, disuccinimidyl suberate, glutardialdehyde, N-succinimidyl-3-(2-pyridyldithio)propionate, N-5-azido-2-nitrobenzoylsuccinimide, N-succinimidyl (4-iodacetyl)-aminobenzoate, a combination of maleinimidohexanoyl-succinimidate and S-acetyl-mercaptosuccinic acid anhydride or analogous compounds come into consideration as chemical linkers.

In a preferred embodiment the oligomeric antibody fragments bind to the same antigen, in an amount sufficient to reduce the Hook effect. according to the invention is provided according to a first aspect of the invention with at least one and optionally several labelling groups. A luminescent metal chelate label is preferred as the label and particularly preferably the oligomeric antibody is ruthenylated i.e. the metal chelate is a ruthenium chelate. The ligands which together with the metal form the metal chelate are usually polydentate ligands i.e. ligands with several coordination positions. Such ligands and metal chelates are described for example in DE-A-44 30 998.8 to the disclosure of which reference is herewith made. The most preferred metal chelates are ruthenium(bipyridyl)$_3$ chelates.

Yet a further aspect of the present invention is a process for the production of an oligomeric antibody which is characterized in that the antibodies or/and fragments thereof are covalently linked together. For this purpose the antibody (fragments) are functionalized in a suitable manner such as by reaction with one of the bifunctional spacer molecules mentioned above. Suitable reaction conditions are generally known in the state of the art and are not stated in detail here (cf. also example 1).

Yet a further aspect of the present invention concerns the use of an oligomeric antibody as defined above as a detection reagent in a sandwich assay. Furthermore the oligomeric antibody can be used to reduce or/and avoid the Hook effect in an immunological method of determination.

Yet a further aspect of the present invention concerns a reagent kit for the immunological determination of an analyte which is suitable for carrying out the method according to the invention. Such a kit comprises in particular a labelled oligomeric antibody as defined above and the second receptor used in the method according to the invention i.e. a solid phase bound receptor or preferably a receptor capable of binding to a solid phase e.g. an antibody or/and antibody fragment. The oligomeric antibody and the second receptor can be present separately in the reagent kit according to the invention or together in a single reagent. The kit optionally contains further reagents such as a suitable solid phase, a substrate solution etc. which are then in general spatially separated.

The method according to the invention is elucidated in more detail by the following examples.

EXAMPLES

Example 1

Production of Biotinylated, Oligomeric and Labelled Antibodies

1. Monomeric Biotinylated Anti-HCG Antibody

Monoclonal anti-HCG-M-1F7.9 IgG (Boehringer Mannheim GmbH) is dissolved in 0.1 M potassium phosphate buffer, pH 8.4 to a concentration of 10 mg/ml. A 6-fold molar amount of biotin-DDS* (dissolved in dimethylsulfoxide; 16.3 mg/ml) is added. After 90 minutes stirring at 25° C. the reaction is stopped by addition of 10 $\mu$l 1 M lysine. It is dialysed against 25 mM potassium phosphate/50 mM NaCl, pH 7.0 and the product is lyophilized.

*Biotin (DDS)=biotinyl-amino-3,6-dioxaoctanyl-aminocarbonylheptanoic acid-N-hydroxysuccinimide ester (see DE 4302241 A1).

2. Oligomeric Ruthenvlated Anti-HCG Antibody a) Ruthenium labelling group

The active ester Ru(bpy)$_3^{2+}$-NHS (ruthenium (2,2'-bipyridyl)$_2$(4-[3-(N-hydroxysuccinimidyl-carboxy) propyl]-4'-methyl-2,2'-bipyridine)$^{2+}$) which can be obtained from the Igen Inc. Co. Rockville USA is used to label antibodies and antibody fragments.

b) Production of anti-HCG-F(ab')$_2$ fragments 300 mg of the monoclonal anti-HCG-M-INN22-IgG antibody is cleaved with pepsin according to Johnstone and Thorpe (Immunochemistry in Practice, page 61 f, Blackwell Scientific, 1987) and the F(ab')$_2$ fragments are purified by S 200 chromatography. Yield: 128 mg F(ab')$_2$.

c) Production and isolation of oligomeric antibody fragments 100 mg anti-HCG-M-INN22 F(ab')$_2$ fragments is dissolved in 1.5 ml 0.15 M K-phosphate buffer, pH 8.3. Shortly before use 27.6 mg disuccinimidyl-suberate (DSS) is dissolved in 1 ml dimethyl-sulfoxide. At intervals of 10 min 5 $\mu$l DSS solution is added to the F(ab')$_2$ solution while stirring.

After a total reaction period of 75 min the cross-linking of the F(ab')$_2$ is stopped with 15 $\mu$l 1 M lysine solution.

The anti-HCG-M-INN22 F(ab')$_2$ crude polymerisate is separated by gel chromatography on Sephacryl S300HR (Pharmacia, Upsala) into fractions with molecular weights of 200,000, 400,000, 500,000–800,000 and >800,000. The polymers of <800,000 are preferred.

d) Production of ruthenylaled oligomeric antibody fragments 5 mg anti-HCG-M-INN22 F(ab')$_2$ oligomer (mol. weight 400,00) is dissolved in 1 ml 0.15 M K-phosphate buffer, 0.15 M NaCl, pH 7.8. Immediately before use 5 mg Ru(bpy)$_3^{2+}$-NHS is dissolved in 0.75 ml anhydrous dimethylsulfoxide. In order to obtain a molar ratio of 3.3:1 based on molecular weights of 1057 for Ru(bpy)$_3^{2+}$-NHS and 100,000 for F(ab')$_2$ monomer, 0.174 mg Ru(bpy)$_3^{2+}$-NHS (59.4 $\mu$l) is added by pipette to the F(ab')$_2$ solution while stirring.

The reaction vessel is incubated for 60 min at 25° C. The reaction is terminated by adding 10 $\mu$l of a 1 M lysine solution.

The mixture is then dialysed for 24 hours against 25 mM K-phosphate buffer/0.1 M NaCl, pH 7.0 and lyophilized.

Yield: 4.4 mg anti-HCG-M-INN22-F(ab')$_2$-Ru(bpy)$_3^{2+}$ oligomer (400,000).

Measurement of the absorbance at 455 nm (ε=13.7) yielded a molar ratio of incorporated label of 2.2–2.8=Ru:F (ab')$_2$.

Oligomeric antibody fragments with molecular weights of 200,000 and 500,000 to 800,000 are coupled in a similar manner to ruthenium labelling groups.

Example 2

Detection of HCG Using Oligomeric Antibodies

The following two solutions containing labelled oligomeric ruthenylated antibodies and monomeric biotinylated antibodies are prepared:

Solution 1:

Monoclonal Ru(bpy)$_3$ labelled anti-HCG F(ab')$_2$ antibody fragments which can be obtained according to example 1 are used as the oligomeric receptor (referred to as AB-BPRU in the following).

AB-BPRU is used with a degree of oligomerization of 5–7 and a degree of ruthenylation of 3.3. In order to prepare solution 1 3.0 μl/ml AB-BPRU is dissolved and mixed in 40 mmol/l phosphate buffer (pH=6.5) containing 0.1% bovine immunoglobulin (IgG), 3.5% bovine serum albumin (BSA) and 150 mmol/l NaCl.

Solution 2:

Monomeric biotinylated anti-HCG antibodies (IgG) are dissolved at a concentration of 5.0 μg/ml, degree of biotinylation=1:10 in an 80 mmol/l phosphate buffer (pH=7.0) containing 0.1% bovine IgG, 2.0% BSA and 150 mmol NaCl.

100 μl solution 1 and 100 μl solution 2 are mixed, 25 μl of the sample to be analysed (human serum) is added and the mixture is incubated for 5 min at 37° C. Afterwards 35 μl of a suspension of streptavidin-coated beads with an iron core, biotin binding capacity 450 to 650 ng/ml, concentration of the solution 720 μg/ml is added and incubated for a further 5 min. The beads are subsequently separated, washed with a solution containing tripropylamine and the electrochemiluminescence is determined. In general Dynabeads M-280 streptavidin (Dynal A. S., Oslo, Norway) are used in the examples as beads i.e. superparamagnetic polystyrene particles with a 2.8 μm diameter to which streptavidin is covalently bound.

The result is that a measuring range up to 12,000 mIU/ml HCG is obtained and a sample containing 500,000 mIU/ml HCG is recognized as being beyond the measuring range (Hook effect). The lower detection limit is <0.1 mIU/ml HCG. In this application the measuring range refers to the range in which undiluted human sera can be correctly determined.

Example 3

Influence of the Degree of Oliqomerization on the Measuring Range

The experimental procedure was as described in example 2, 3.13 μg/ml AB-BPRU being used in solution 1 which differed in their degrees of oligomerization as follows:

| | | |
|---|---|---|
| P1 | MW> | 800,000 |
| P2 | | 500,000–800,000 |
| P3 | | 400,000 |
| P4 | | 200,000 |
| P5 | | 100,000 (=F(ab')$_2$ |

The results are shown in Table 1. It can be seen that as the degree of cross-linking increases (=molecular weight) the signals of the higher standards increase whereas the blank value (signal of the zero standard a) remains constant. Hence the sensitivity of the test increases i.e. the increase in the degree of oligomerization leads to a wider measuring range while retaining the lower limit of detection.

TABLE 1

| Anti-body | Signal Standard a (counts × 1000) | Signal Standard e (counts × 1000) | Signal Hook sample (counts × 1000) | Standard e/ Standard a |
|---|---|---|---|---|
| P1 | 15 | 16,470 | 14,348 | 1098 |
| P2 | 15 | 12,887 | 12,444 | 859 |
| P3 | 14 | 11,589 | 13,034 | 828 |
| P4 | 13 | 8,714 | 13,000 | 670 |
| P5 | 12 | 6912 | 10,929 | 576 |

Example 4

Detection of HCG Using a Monomeric Monoclonal Antibody (comparison), Addition of Unlabelled Antibody In this example according to the method of U.S. Pat. No. 4,743,542 a monomeric monoclonal antibody MAB<HCG>-BPRU with a degree of ruthenylation of 1:8 is used at a concentration of 2 μg/ml in solution 1 and the biotinylated monoclonal antibody in solution 2 is used at a concentration of 2 μg/ml. In addition different amounts (2, 4, 8 and 16 μg/ml) of an unlabelled monomeric monoclonal anti-HCG antibody are added to the test solution so that this antibody is present in the test mixture at concentrations of 2, 4, 8 and 16 μg/ml. 3 Human sera with different HCG concentrations are tested, HS1 (2941 mIU/ml), HS2 (50,000 mIU/ml) and HS3 (500,000 mIU/ml, Hook sample) as well as 2 standards containing 0.0 (standard a) and 13.0 mIU/ml (standard b) HCG. The results are summarized in Table 2.

TABLE 2

| | unlabelled monomeric anti-HCG antibody [μg/ml] | | | |
|---|---|---|---|---|
| | 2 | 4 | 8 | 16 |
| increase of the measuring range* | ≡1.0 | 1.84 | 2.76 | 4.19 |
| standard b/standard a | 1.89 | 1.77 | 1.58 | 1.44 |

*Quotient of the measuring range at the respective concentration of unlabelled antibody divided by the measuring range with 2 μg/ml unlabelled antibody.

It was found that the measuring range increases with an increasing amount of unlabelled antibody. At the same time the signal of the standard b decreases as well as that of the other human sera whereas that of the standard a (zero serum, blank value) remains essentially constant. Consequently there is an increasing worsening of the differentiation in the lower part of the measuring range. The quotient standard b/a which should be at least in the range of 1.9 to 2.0 for a reliable diagnosis is already below this value when 2 μg/ml unlabelled antibody is added. A statement about a possible pregnancy cannot be made.

Example 5

Detection of HCG with Monomeric Polyclonal Antibody (comparison), Addition of unlabelled Antibody The procedure is as in example 4 except that the polyclonal antibody PAB<β—HCG>S—(PA)—IgG(DE) was used as the unlabelled antibody. The results correspond essentially to those of example 4, but the measuring range is only increased by a factor of 1.35. A reliable differentiation is not possible in the lower signal range. The quotient standard b/a was 1.33 when 2 μg/ml of the unlabelled PAB was added and decreases further at higher PAB concentrations (16 μg/ml: b/a=0.94).

Example 6

Detection of HCG with Oligomeric Monoclonal Antibody Addition of Unlabelled Antibody The procedure is according to example 2 in which a ruthenylated oligomeric antibody (degree of oligomerization ca. 4–8) according to the invention was used as the detection antibody at a concentration of 1, 2 and 4 μg/ml. The results are summarized in Table 3.

TABLE 3

|  | ruthenylated oligomeric anti-HCG antibody [μg/ml] | | |
| --- | --- | --- | --- |
|  | 1 | 2 | 4 |
| increase of the measuring range* | ≡1.0 | 1.83 | 4.19 |
| standard b/standard a | 3.07 | 1.98 | 2.24 |

*Quotient of the measuring range at the respective concentration of unlabelled antibody divided by the measuring range with 1 μg/ml unlabelled antibody.

The blank value (standard a) as well as the signal level of the other samples (human sera and standards) increase with an increasing AB-BPRU concentration. As can be seen from the table the quotient standard b/a remains at or above 2.0 and hence ensures a good measurement in the lower concentration range. At the same time the measuring range is considerably increased with an increasing AB-BPRU concentration which in the present example runs almost proportional (a doubling of the antibody concentration corresponds approximately to a doubling of the measuring range).

Since the measuring range is increased while retaining the accuracy of the measurement in the lower HCG concentration range, in this case there is an actual extension of the measuring range to a full extent.

Example 7

Detection of TSH Comparison of Oligomeric and Monomeric Monoclonal Antibody

The TSH test is used to diagnose the thyroid function. Increased as well as greatly reduced TSH values in serum are of diagnostic importance. For this reason a high precision of the test is also important in the lower range as well as a good differentiation between the low standard a and the second lowest b. The ratio e/a, the quotient of the highest divided by the lowest standard, serves as a parameter for the entire measuring range. The quotient should be as high as possible. The following reagents were used in a similar system to that used for HCG:

R1: Phosphate buffer, 50 mmol, pH=7.4; 0.1% each of MIT and oxyperoin (for preservation), 2% bovine serum albumin, 1% bovine IgG and ruthenylated monoclonal antibody MAB<TSH>—m—Fab—BP—Ru at a concentration of 2.0 μg/ml for the oligomer and 0.2–1.0 μg/ml for the monomer.

R2: Reagent as in R1, biotinylated monomeric antibody MAB<TSH>F(ab')b-Bi(DDS) being used instead of MAB-BPRU at a concentration of 1.7 μg/ml.

Beads: Microparticles with an iron core are used having a biotin binding capacity of 700 μg/ml.

The reaction is carried out by pipetting together 70 μl sample, 80 μl R1 and 80 μl R2, carefully mixing and incubating for 10 min. Afterwards 50 μl beads is added and it is incubated for a further 10 min.

Afterwards the reaction mixture is placed on the electrode as described for HCG, the microparticles are held with the aid of a magnet and washed. This is followed by the electrochemical reaction in which the light signal is measured quantitatively.

The result is shown in Table 4.

TABLE 4

| | oligomeric antibody [μg/ml] | monomeric antibody [μg/ml] | | | | | | |
| --- | --- | --- | --- | --- | --- | --- | --- | --- |
| | 2.0 | 1.0 | 0.9 | 0.8 | 0.7 | 0.6 | 0.4 | 0.2 |
| Std a* | 37543 | 34012 | 31954 | 31070 | 29198 | 25816 | 21138 | 16650 |
| std b* | 95864 | 61184 | 59993 | 58455 | 57041 | 50877 | 42776 | 30803 |
| Std e* | 10459454 | 5124952 | 5163815 | 5080088 | 4894581 | 4690125 | 4030587 | 2770455 |
| b/a | 2.55 | 1.80 | 1.88 | 1.88 | 1.95 | 1.97 | 2.02 | 1.88 |
| e/a | 279 | 151 | 162 | 164 | 167 | 182 | 19 | 166 |
| b-a | 58311 | 27172 | 27979 | 27386 | 27843 | 26161 | 21638 | 14263 |

*mean of 3 measurements

Increasing concentrations of monomeric AB-RU increase the signal of the standard a as well as that of the standard e. The quotient b/a remains almost constant, an improvement of the resolving power in the lower range (b-a) is not achieved and the dynamics of the measuring range are not improved (e/a almost constant). This is only achieved when oligomeric AB-RU is added. Similar results are obtained for other lots of microparticles.

The precision and accuracy of the measurement is improved by the use of oligomeric AB which can also be seen in method comparisons.

Example 8

Detection of HCG with an Oligomeric Antibody With/Without Addition of Unlabelled Antibody (F $(ab')_2$ R1: 3.0 μg/ml MAB<HCG>-ruthenium(II)tris-(bipyridyl)-NHS-oligo as $F(ab')_2$, degree of polymerization 5–7, degree of ruthenylation 3.3 is dissolved and mixed in a 40 mmol/l phosphate buffer, pH=7.5 which additionally contains 0.1% bovine IgG and 3% bovine serum albumin (BSA).

R2: 5.0 μg/ml MAB<HCG>-IgG-blotinylated with a degree of biotinylation of 1:10 is used in a reagent as described above instead of MAB-PBRU.

R3: 4 μg/ml unlabelled polyclonal PAB<HCG>-IgG is additionally added to a reagent R1 and mixed.

A series of HCG standards with concentrations of 0 to 20,000 mIU/ml are analysed in the experimental system as described in example 7 without (R1, R2, beads) and with addition (R2, R3, beads) of unlabelled monoclonal antibody.

It turns out that a flatter calibration curve is obtained when reagents R2 and R3 are used than when R1 and R2 are used. However, the measuring range is larger in the system R2, R3 (addition of unlabelled antibody).

What is claimed is:

1. A method for extending the concentration range at which an analyte can be detected in a sample liquid according to the principle of a sandwich assay comprising the step of a) incubating the sample liquid in the presence of a solid phase with at least two receptors that are each capable of binding to the analyte wherein the first receptor is soluble and the second receptor (i) is bound to a solid phase or (ii) is capable of binding to a solid phase; and b) detecting the analyte by determining a label in the solid phase, the liquid phase, or both the solid phase and the liquid phase, wherein the first receptor is a labeled oligomer of a binding molecule selected from antibodies, antibody fragments, and mixtures thereof, and wherein all of said antibodies and antibody fragments bind to the same antigen, in an amount sufficient to reduce the Hook Effect.

2. Method as claimed in claim 1, wherein the degree of oligomerization of the first receptor is 2 to 15.

3. Method as claimed in claim 1, wherein the first receptor carries 1 to 20 labelling groups.

4. Method as claimed in claim 3, wherein the first receptor carries 2 to 10 labelling groups.

5. Method as claimed in claim 3, wherein the labelling group is a luminescent metal chelate labelling group.

6. Method as claimed in claim 5, wherein the luminescent metal chelate is selected from the group consisting of ruthenium, rhenium, iridium andosmium chelates.

7. Method as claimed in claim 6, wherein the luminescent metal chelate is a ruthenium chelate.

8. The method as claimed in claim 1, wherein the solid phase is composed of a particulate, magnetic material and is coated with the second receptor or a material which is capable of binding to the second receptor.

9. Method as claimed in claim 1, wherein the determination is carried out in the presence of a labelled first receptor and additional unlabelled analyte-specific receptor.

10. Method of claim 1 wherein the second receptor carries biotin groups and the solid phase carries avidin or streptavidin groups.

11. Method for reducing Hook effect in an immunoassay, comprising carrying out said immunoassay with an oligomeric antibody, wherein said oligomeric antibody comprises a covalently linked conjugate of at least two antibodies, antibody fragments, and/or mixtures therof, the degree of oligomerization being 2–15, wherein all of said antibodies and antibody fragments bind to the same antigen, in an amount sufficient to reduce the Hook effect.

12. The method of claim 11, wherein said conjugate of at least two antibodies, antibody fragments and mixtures thereof are directly linked by a chemical bond.

13. The method of claim 11, wherein said conjugate of at least two antibodies, antibody fragments and/or mixture thereof are linked by a bifunctional linker or spacer molecule.

14. The oligomeric antibody of claim 13, wherein said bifunctional spacer or linker molecule is bis(maleinimido)-methyl ester, dimethyl suberimidate, disuccinimidyl suberate, glutardialdehyde, N-succinimidyl-3-(2-pyridyldithio) propionate, N-5-azido-2-nitrobenzoylsuccinimide, N-succinimidyl (4-iodacetyl)-aminobenzoate, or a combination of maleinimidohexanoyl-succinimidate and S-acetyl-mercaptosuccinic acid anhydride.

15. Method of claim 11 wherein said oligomeric antibody comprises 4 or more paratopes, and wherein said oligomeric antibody carries at least one labeling group.

16. Method of claim 15 wherein the labelling groups are luminescent metal chelate labelling groups.

17. Method of claim 16 wherein the luminescent metal chelate is a ruthenium chelate.

18. Method of claim 15 wherein said oligomeric antibody carries between 2 to 20 labeling groups.

19. Method of claim 11 wherein said oligomeric antibodies comprises antibodies or/and fragments thereof covalently linked to one another.

* * * * *